US009657070B2

(12) United States Patent
Gronlund et al.

(10) Patent No.: US 9,657,070 B2
(45) Date of Patent: May 23, 2017

(54) RECOMBINANT ALLERGEN

(71) Applicant: ALK-Abello A/S, Horsholm (DK)

(72) Inventors: Hans Gronlund, Lidingo (SE);
Marianne van Hage, Bromma (SE)

(73) Assignee: ALK-ABELLO A/S, Horsholm (DK)

( * ) Notice: Subject to any disclaimer, the term of this patent is extended or adjusted under 35 U.S.C. 154(b) by 0 days.

(21) Appl. No.: 13/772,046

(22) Filed: Feb. 20, 2013

(65) Prior Publication Data
US 2013/0195902 A1 Aug. 1, 2013

Related U.S. Application Data

(63) Continuation of application No. 10/554,409, filed as application No. PCT/IB2004/001583 on Apr. 22, 2004, now abandoned.

(30) Foreign Application Priority Data

Apr. 24, 2003 (GB) .................................. 0309345.7

(51) Int. Cl.
*A61K 39/00* (2006.01)
*A61K 39/35* (2006.01)
*A61K 39/36* (2006.01)
*C07K 1/00* (2006.01)
*C07K 14/00* (2006.01)
*C07K 17/00* (2006.01)
*C07K 14/47* (2006.01)

(52) U.S. Cl.
CPC .............. *C07K 14/47* (2013.01); *A61K 39/00* (2013.01); *C07K 2319/00* (2013.01)

(58) Field of Classification Search
None
See application file for complete search history.

(56) References Cited

U.S. PATENT DOCUMENTS

| 6,048,962 A | 4/2000 | Gefter et al. |
| 2002/0164342 A1 | 11/2002 | Guyre et al. |

FOREIGN PATENT DOCUMENTS

WO  WO 00/20032 A1  4/2000

OTHER PUBLICATIONS

Kaiser et al. 'Crystallization and preliminary crystallographic data of a Fel d 1 (1+2) construct corresponding to the major allergen from cat.' Acta Cryst. F61: 232-234, 2005.*
Abaza et al., "Effects of amino acid substitutions outside an antigenic site on protein binding to monoclonal antibodies of predetermined specificity obtained by peptide immunization: demonstation with region 94-100 (antigenic site 3) of myglobin." *Journal of Protein Chemistry*. 11(5):443-444, 1992.
Blumenthal et al., "Definition of an Allergen." *Allergens and Allergen Immunotherapy*. Ed. R Lockey, S. Bukantz and J. Bousquet. New York: Marcel Decker, 2004.37-50.
Colman et al., "Effects of amino acid sequence changes on antibody-antigen interactions." *Research in Immunology*. 145(1):33-36, 1994.
George et al., "An Analysis of Protein Domain Linkers: Their Classification and Role in Protein Folding." *Protein Engineering*. 15(11): 871-879, 2003.
Gronlund, Hans et al., "Formation of Disulfide Bonds and Homodimers of the Major Cat Allergen Fel d 1 Equivalent to the Natural Allergen by Expression in *Escherichia coli*," *The Journal of Biological Chemistry*, 2003, pp. 40144-40151, vol. 278, No. 41. The American Society for Biochemistry and Molecular Biology, Inc.
Maleki et al., "The effects of roasting on the allergenic properties of peanut proteins." *Journal of Allergy and Clinical Immunology*. 763-768, 2000.
Rogers, Bruce L., et al., "Recombinant *Fel d* I: Expressions, Purification, IgE Binding and Reaction with Cat-Allergic Human T Cells," *Molecular Immunology*, 1993, pp. 559-568, vol. 30, No. 6. Pergamon Press Ltd.
Vailes, Lisa D, et al., "High-level expression of immunoreactive recombinant cat allergen (Fel d 1): Targeting to antigen-presenting cells," *J Allergy Clin Immunol.*, Nov. 2002, pp. 757-762, vol. 110, No. 5.
Batard, T., et al., "Demonstration of a partially cryptic epitope of the major cat allergen Fel d 1: Consequences for mAb-based standardization of cat extracts," *J Allergy Clin Immunol*, 2000, vol. 106(4), pp. 669-676.
Bond, J., et al., "Native and Recombinant Fel dI As Probes Into the Relationship of Allergen Structure to Hnuman IgE Immunoreactivity," *Molecular Immunology*, 1993, vol. 30(16), pp. 1529-1541.
Chapman, M., et al., "Monoclonal antibodies to the major feline allergen Fel d I. II. Single step affinity purification of Fel d I, N-terminal sequence analysis, and development of a sensitive two-site immunoassay to assess Fel d I exposure," *The Journal of Immunology*, 1988, vol. 140, pp. 812-818.
Counsell, C., et al., "Allergens IgE, mediators, inflammatory mechanisms," *J Allergy Clin Immunol*, 1996, vol. 98(5, Part 1), pp. 884-894.
Duffort, O., et al, "Studies of the Biochemical Structure of the Major at Allergen FELIS DOMESTICUS I," *Molecular Immunology*, 1991, vol. 28(4/5), pp. 301-309.
Griffith, I., et al., "Expression and genomic structure of the genes encoding Fd1, the major allergen from the domestic cat," *Gene*, 1992, vol. 113, pp. 263-268.

(Continued)

*Primary Examiner* — Nora Rooney
(74) *Attorney, Agent, or Firm* — Womble Carlyle Sandridge & Rice LLP

(57) ABSTRACT

Dander from the domestic cat (*Felis domesticus*) is one of the most common causes of IgE mediated allergy. The present invention relates to a recombinant folded Fel d 1 with molecular and biological properties similar to the natural counterpart and specifically a synthetic gene coding for a direct fusion of Fel d 1 chain 2 N-terminally to chain 1. *E coli* expression resulted in a non-covalently associated homodimer with an apparent molecular weight of 30 kDa defined by size exclusion chromatography, each 19177 Da subunit displayed a disulfide pattern identical to that found in the natural Fel d 1, and having identical fold of natural and recombinant Fel d 1. The, recombinant Fel d 1 provides for diagnosis and allergen specific immunotherapy of cat allergy.

17 Claims, 9 Drawing Sheets

(56) References Cited

OTHER PUBLICATIONS

Hedlin, G., et al., "Immunotherapy with cat-and dog-dander extracts," *J Allergy Clin Immunol*, 1991, vol. 87(5), pp. 955-964.

Ichikawa, K., et al., "High prevalence of sensitization to cat allergen among Japanese children with asthma, living without cats," *Clinical and Experimental Allergy*, 1999, vol. 29, pp. 754-761.

Keating, K., et al., "Enhanced Immunoreactivity and Preferential Heterodimer Formation of Reassociated Fel d I Recombinant Chains," *Molecular Immunology*, 1995, vol. 32(4), pp. 287-293.

Kristensen, A., et al., "Determination of Isoforms, N-Linked Glycan Structure and Disulfide Bond Linkages of the Major Cat Allergen Fel d1 by a Mass Spectrometric Approach," *Biol. Chem.*, 1997, vol. 378, pp. 899-908.

Lau, S., et al., "Early exposure to house-dust mite and cat allergens and development of childhood asthma: a cohort study," *The Lancet*, 2000, vol. 365, pp. 1392-1397.

Leitermann, K., et al., "Cat allergen 1: Biochemical, antigenic, and allergenic properties," *J. Allergy Clin. Immunol.*, 1984, vol. 74(2), pp. 147-153.

Lilja, G., et al., "Immunotherapy with cat- and dog-dander extracts," *J. Allergy Clin. Immunol.*, 1989, vol. 83(1), pp. 37-44.

Milligen, F., et al., "IgE epitopes on the cat (*Felis domesticus*) major allergen Fel d 1: A study with overlapping synthetic peptides," *J Allergy Clin Immunol*, 1994, vol. 93(1, Part 1), pp. 34-43.

Morgenstern, J., et al., "Amino acid sequence of Fel dI, the major allergen of the domestic cat: Protein sequence analysis and cDNA cloning," *Proc. Natl. Acad. Sci. USA*, 1991, vol. 88, pp. 9690-9694.

Norman, P., et al., "Treatment of Cat Allergy with T-cell Reactive Peptides," *Am J Respir Crit Care Med*, 1996, vol. 154, pp. 1623-1628.

Ohman, J., et al., "Allergens of Mammalian Origin," *The Journal of Immunology*, 1974, vol. 113(6), pp. 1668-1677.

Ohman, J., et al., "IgE antibody to cat allergens in an allergic population," *J. Allergy Clin. Immunol.*, 1977, vol. 60(5), pp. 317-323.

Oldfield, W., et al., "Effect of T-cell peptides derived from Fel d 1 on allergic reactions and cytokine production in patients sensistive to cats: a randomised controlled trial," *The Lancet*, 2002, vol. 360, pp. 47-53.

Roost, H., et al., "Role of current and childhood exposure to cat and atopic sensitization," *J Allergy Clin Immunol*, 1999, vol. 104(5), pp. 941-947.

Slunt, J., et al., "IgE antibodies to recombinant forms of Fel d 1: Dichotomy between fluid-phase and solid-phase binding studies," *J Allergy Clin Immunol*, 1995, vol. 95(6), pp. 1221- 1228.

Vailes, L., et al., "Fine specificity of B-cell epitopes on *Felis domesticus* allergen 1 (Fel d 1): Effect of reduction and alkylation or deglycosyllation on Fel d 1 structure and antibody binding," *J Allergy Clin Immunol*, 1994, vol. 93(1, Part 1), pp. 22-33.

Van Ree, R., et al, "Purified natural and recombinant Fel d 1 and cat albumin in in vitro diagnostics for cat allergy," *J Allergy Clin Immunol*, 1999, vol. 104(6), pp. 1223-1230.

Van'T Hof, W., et al., "Epitope mapping of the cat (*Felis dotnesticus*) major allergen Fel d 1 by overlapping synthetic peptides and monoclonal antibodies against native and denatured Fel d 1," *Allergy*, 1993, vol. 48, pp. 255-263.

* cited by examiner

```
  0 Met-Val-Lys-Met-Ala-Glu-Thr-Cys-Pro-Ile-Phe-Tyr-Asp-Val-Phe-Phe-Ala-Val-Ala-
 19 Asn-Gly-Asn-Glu-Leu-Leu-Leu-Asp-Leu-Ser-Leu-Thr-Lys-Val-Asn-Ala-Thr-Glu-Pro-
 38 Glu-Arg-Thr-Ala-Met-Lys-Lys-Ile-Gln-Asp-Cys-Tyr-Val-Glu-Asn-Gly-Leu-Ile-Ser-
 57 Arg-Val-Leu-Asp-Gly-Leu-Val-Met-Thr-Thr-Ile-Ser-Ser-Ser-Lys-Asp-Cys-Met-Gly-
 76 Glu-Ala-Val-Gln-Asn-Thr-Val-Glu-Asp-Leu-Lys-Leu-Asn-Thr-Leu-Gly-Arg- Glu-Ile-
 95 Cys-Pro-Ala-Val-Lys-Arg-Asp-Val-Asp-Leu-Phe-Leu-Thr-Gly-Thr-Pro-Asp-Glu-Tyr-
114 Val-Glu-Gln-Val-Ala-Gln-Tyr-Lys-Ala-Leu-Pro-Val-Val-Leu-Glu-Asn-Ala-Arg-Ile-
133 Leu-Lys-Asn-Cys-Val-Asp-Ala-Lys-Met-Thr-Glu-Glu-Asp-Lys-Glu-Asn-Ala-Leu-Ser-
152 Leu-Leu-Asp-Lys-Ile-Tyr-Thr-Ser-Pro-Leu-Cys-Leu-Glu-His-His-His-His-His-His
```

FIGURE 1

RECOMBINANT ALLERGEN

CROSS-REFERENCE TO RELATED APPLICATIONS

This application is a continuation of U.S. application Ser. No. 10/554,409, filed Apr. 23, 2008, which is a filing under 35 USC 371 of PCT/IB2004/001583, filed Apr. 22, 2004, which claims priority from GB 0309345.7, filed Apr. 24, 2003, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 430227SEQLIST.txt, created on Feb. 20, 2013, and having a size of 14 KB and is filed concurrently with the specification. The sequence listing contained in this ASCII formatted document is part of the specification and is herein incorporated by reference in its entirety.

This invention relates to a recombinant allergen and in particular to a recombinant Fel d 1, the major cat allergen, which is functionally equivalent to the natural allergen.

Exposure to airborne particles derived from household cats (Fells domesticus) is a common cause of IgE-mediated allergy in, for example, Europe and the US (see Ichikawa, K., et al. (1999) *Clin Exp Allergy* 29, 754-761; Roost, H. P., et al. (1999) *J Allergy Clin Immunol* 104, 941-947 and Lau, S., et al. (2000) *Lancet* 356, 1392-1397). Indeed, cats are found in about 25% of households in Western countries and allergy to cats is found in a large part of the population, e.g. about 10% in the US. The severity of symptoms range from relatively mild rhinitis and conjunctivitis to potentially life-threatening asthmatic exacerbation.

Treatment of cat allergy by allergen injections is often employed but clinical results are variable since for cat allergy, only crude dander extract is available for treatment (see Lilja, G., et al. (1989) *J Allergy Clin Immunol* 83, 37-44 and Hedlin, G., et al. (1991) *J Allergy Clin Immunol* 87, 955-964) although alternative formulations have been proposed (see Norman, P. S., et al. (1996) *Am J Respir Crit Care Med* 154, 1623-1628 and Oldfield, W. L., et al. (2002) *Lancet* 360, 47-53).

Although patients are occasionally sensitised to several different molecules in cat dander and pelts, e.g. albumin and cystatin, the major allergen is Fel d 1 (i.e. *Felis domesticus* allergen 1, formerly termed Cat 1). The importance of this allergen has been emphasised in numerous studies. In fact more than 80% of cat allergic patients exhibit IgE antibodies to this potent allergen (see Ohman, J. L., Jr., et al. (1977) *J Allergy Clin Immunol* 60, 317-323 and van Ree, R., et al. (1999) *J Allergy Clin Immunol* 104, 1223-1230).

Fel d 1, was first described 25 years ago as the dominant cat allergen and several subsequent studies have characterised the biochemical and immunological nature of Fel d 1 (see Ohman, J. L., Jr., et al. (1974) *J Immunol* 113, 1668-1677; Leitermann, K., et al. (1984) *J Allergy Clin Immunol* 74, 147-153; Chapman, M. D., et al. (1988) *J Immunol* 140, 812-818; Duffort, O. A., et al. (1991) *Mol Immunol* 28, 301-309; Morgenstern, J. P., et al. (1991) *Proc Natl Acad Sci USA* 88, 9690-9694; van't Hof, W., et al. (1993) *Allergy* 48, 255-263; van Milligen, F. J et al. (1994) *J Allergy Clin Immunol* 93, 34-43; Vailes, L. D., et al. (1994) *J Allergy Clin Immunol* 93, 22-33; Counsell, C. M., et al. (1996) *J Allergy Clin Immunol* 98, 884-894; Kristensen, A. K., et al. (1997) *Biol Chem* 378, 899-908 and Batard, T., et al. (2000) *J Allergy Clin Immunol* 106, 669-676).

The allergen is a 35-39 kDa acidic glycoprotein containing 10-20% N-linked carbohydrates and is found in the pelt; saliva and lachrymal glands of cats. It is formed by two noncovalently linked heterodimers, each consisting of one 70 residue peptide (known as "chain 1") and one 85, 90 or 92 residue peptide (known as "chain 2") encoded by separate genes (see Duffort, O. A., et al. (1991) *Mol Immunol* 28, 301-309; Kristensen, A. K., et al. (1997) *Biol Chem* 378, 899-908; Morgenstern, J. P., et al, (1991) *Proc Natl Acad Sci USA* 88, 9690-9694 and Griffith, I. J., et al. (1992) *Gene* 113, 263-268). (Chain 1 shares limited (30%) sequence homology with rabbit uteroglobulin/human Clara cell 10 kDa protein (CC10) and the mature natural (n)Fel d 1 has been associated with gelatin and fibronectin degrading activity.)

Several variants of Fel d 1 have been observed and are reported in the references cited hereinabove. The primary structure of chain 1 is the sequence of SEQ ID NO 1. Reported variants of chain 1 are $Lys_{29} \rightarrow Arg$ or Asn and $Val_{33} \rightarrow Ser$. The primary structure of chain 2 is the sequence of SEQ ID NO 2 or 3. Reported variants of chain 2 are $Asn_{19} \rightarrow Ser$, $Gly_{20} \rightarrow Leu$, $Ile_{55} \rightarrow Val$, $Arg_{57} \rightarrow Lys$, $Val_{58} \rightarrow Phe$, $Glu_{69} \rightarrow Val$, $Tyr_{72} \rightarrow Asp$, $Gln_{79} \rightarrow Glu$ and $Asn_{88} \rightarrow Lys$ (see Kristensen, A. K, et al. (1997) *Biol Chem* 378, 899-908).

Furthermore, three inter-chain disulfide bridges linking the two peptides in native Fel d 1 have been identified, i.e. $^3Cys(1)$-$^{73}Cys(2)$, $^{44}Cys(1)$-$^{48}Cys(2)$ and $^{70}Cys(1)$-$^7Cys(2)$, suggesting an anti-parallel orientation of Fel d 1 peptides. See Kristensen, A. K., et al. (1997) *Biol Chem* 378, 899-908.

Several attempts have been made to associate the separate peptides into a native-like allergen in *E coli* with only partial success (see Bond, J. F., et al. (1993) *Mol Immunol* 30, 1529-1541; Keating, K. M., et al. (1995) *Mol Immunol* 32, 287-293 and Slunt, J. B., et al. (1995) *J Allergy Clin Immunol* 95, 1221-1228) and recently a soluble and immunoreactive chain 1-linker-chain 2-fusion expressed in baculovirus has been described in which the linker is a peptide having 19 amino acid residues.

A mix of the separate chains has proven to be useful for in vitro allergy diagnosis, but so far no soluble, stable and correctly folded recombinant (r)Fel d 1 homodimer with retained disulfide formation has been available (see van Ree, R., et al. (1999) *J Allergy Clin Immunol* 104, 1223-1230 and Slunt, J. B., et al. (1995) *J Allergy Clin Immunol* 95, 1221-1228).

Accordingly, the present invention provides a recombinant Fel d 1 fusion product comprising a Fel d 1 chain 1, a Fel d 1 chain 2 and a linker selected from a carbon-nitrogen bond or a short peptide linker which links the N-terminal amino acid of one chain to the C-terminal amino acid of the other chain.

The present invention will now be described with reference to the following drawings, in which FIG. 1 shows the primary structure and disulfide bridges of the recombinant His-tagged rFel d 1(2+1) fusion molecule [SEQ ID NO: 35];

Figure 2:
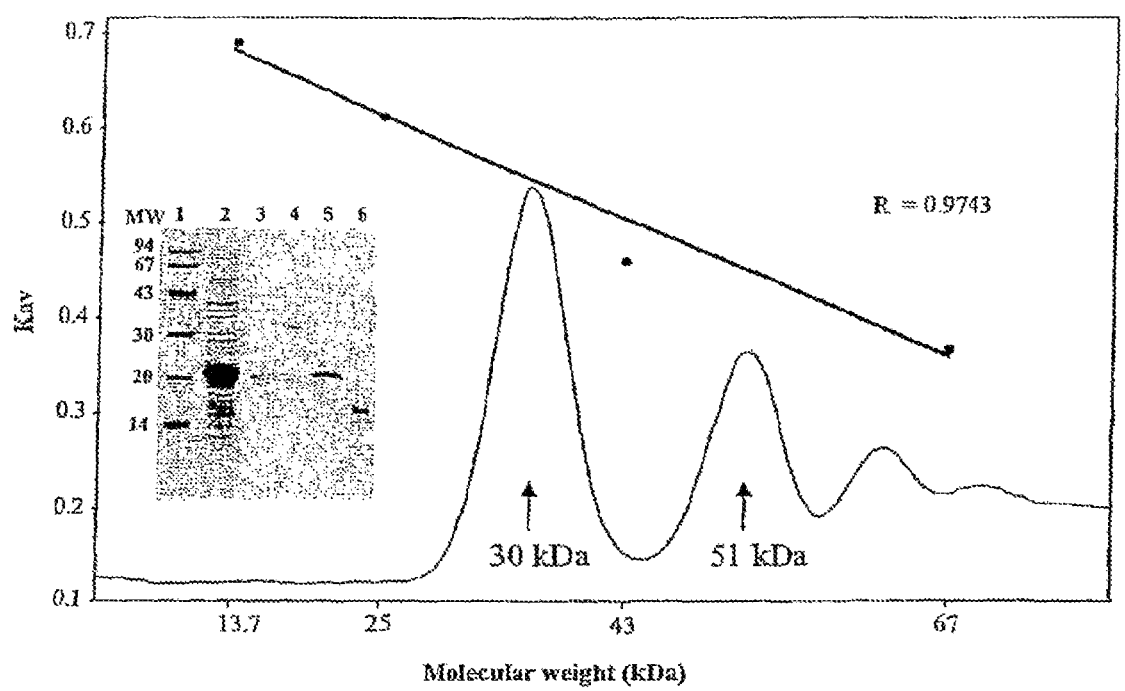
FIG. 2 shows the results of size exclusion chromatography of rFel d 1(2+1)

The present invention demonstrates that a protein derived from a fusion of the genes coding for the two polypeptide chains constituting Fel d 1 can be folded to resemble closely the structure and allergenic activity of natural (n)Fel d 1. Surprisingly, it has been found that such a recombinant protein mimics the structure and allergenic activity of nFel d 1 when the two peptide chains are linked by a carbon-nitrogen bond or a short peptide linker. Synthetic genes coding for the two Fel d 1 chains may be produced using known techniques, for example by PCR by overlapping oligonucleotides and expression as refolded His-tagged proteins in *E coli*. Two possible constructs, namely one with chain 1 and the other with chain 2 in the N-terminal position, are exemplified. Both constructs have been purified to homogeneity and analysed, in particular for intra-molecular disulfide bridges and homodimer formation using techniques such as size exclusion chromatography, mass spectrometry and surface plasmon resonance.

As explained hereinabove, the two polypeptide chains constituting nFel d 1 are known and described extensively in the prior art. The sequence of chain 1 of nFel d 1 is as shown in SEQ ID NO 1 and the sequence of chain 2 is as shown in SEQ ID NO 2 or 3. However, as well as the variants described hereinabove, any homologous peptide or peptide fragment which has substantially the same sequence and/or provides substantially the same function in the rFel d 1 as chain 1 or chain 2 of nFel d 1 may be used in the present invention. The homologues or fragments of chain 1 or chain 2 must provide substantially the same allergenic activity in the rFel d 1 of the present invention as in nFel d 1. Allergenic activity may be measured by any of the known techniques in the art, such as the response to IgE. Preferably no significant difference in response to IgE between the recombinant and natural Fel d 1 is observed. Preferably the homologues should also provide for the adoption of substantially the same conformation as in nFel d 1.

The linker which links chain 1 and chain 2 is a key feature of the present invention. Although attempts have been made to provide a rFel d 1 using chains 1 and 2 from nFel d 1 with a linker, such efforts have been unsuccessful. The present applicant has found, however, that rFel d 1 which mimics the properties of nFel d 1 may be obtained by linking chain 1 and chain 2 with a linker selected from a carbon-nitrogen bond and a short peptide, i.e. having from 1 to 9, preferably 1 to 5, particularly preferably 1 to 3 amino acids. Surprisingly, a bond or a short peptide does not induce significant constraints or unfolding, as shown by comparison with nFel d 1 in circular dichroism (CD) measurements.

Preferably the linker is a carbon-nitrogen bond thereby providing a direct fusion between chain 1 and chain 2. An advantage of direct fusion is that no extra amino acids are included within the molecule which otherwise might compromise the use of the molecule in diagnosis and treatment. However, a short (1 to 9 amino acids) peptide bond may be tolerated. An advantage of including a short peptide chain is that the linker may then be used as a target site for a reagent, such as an enzyme, capable of selectively cleaving the polypeptide at the linker. By selective, the applicant means that the polypeptide is cleaved at the linker rather than within chain 1 or chain 2. Such a cleavage would then provide a rFel d 1 having substantially the same structure as nFel d 1, i.e. in which chain 1 and chain 2 are covalently bonded together only by the disulfide bridges.

The present invention therefore also provides a process for preparing a recombinant Fel d 1 peptide comprising the steps of synthesising the peptide having the linker as described herein and selectively cleaving the polypeptide at the linker, using, a suitable reagent and preferably an enzyme. Such reagents and enzymes are well known in the art.

The linker links the N-terminal amino acid of one chain to the C-terminal amino acid of the other chain. Preferably the linker links the N-terminal amino acid of chain 1 to the C-terminal amino acid of chain 2 providing a so-called (2+1) construct. Thus, rFel d 1(1+2) contains chain 1 and chain 2 in which the C-terminal of chain 1 is fused to the N-terminal of chain 2 and rFel d 1(2+1) contains chain 1 and chain 2 in which the N-terminal of chain 1 is fused to the C-terminal of chain 2 as shown in FIG. 1 and SEQ ID NO 4. Both chains show specific IgE reactivity although results suggest that rFel d 1(2+1) exhibits superior IgE reactivity to rFel d 1(1+2).

As well as the linker described hereinabove, chains 1 and 2 of the rFel d 1 of the present invention will also be linked by one or more disulfide bridges on account of the presence of cysteine residues in each chain. Biological recognition of proteins is dependent on the primary structures, displayed as linear T cell epitopes in the cavity of MHC molecules on antigen presenting cells. Equally important for the biological functions are the three-dimensional structures, which in turn depends on secondary structure and frequently on correct and stable disulfide bridges. The rFel d 1 should have at least one disulfide bridge and preferably 2 or 3, particularly preferably 3, as in nFel d 1. The applicant has analysed rFel d 1(2+1) by CD measurements and determined the intra-chain disulfide linking through trypsin cleavage and mass spectrometry. The secondary structure and disulfide bridges pattern of nFel d 1 as well as the proliferation of cultured PBMC in the presence of nFel d 1 were found to correspond well to those observed for rFel d 1(2+1). Thus, the rFel d 1 forms a basis for a stable and immunoreactive allergen.

An important structural feature of nFel d 1 is the formation of stable non-covalently associated homodimers. The ability of rFel d 1(2+1) to form homodimers has been investigated by several methods, including CD spectroscopy and analysis of IgE antibody responses in direct and competition ELISA using sera from individuals sensitised to cat was carried out. The biological activity was demonstrated by the induction of CD203c on basophils of cat allergic patients.

The 30 kDa rFel d 1(2+1) fraction isolated by size exclusion chromatography (SEC) indicates a homodimer by virtue of its elution position and corresponding molecular weight. The difference in molecular weight to the cat dander derived 35-38 kDa nFel d 1 may be explained by the presence of 10-20% N-linked carbohydrates in the natural allergen. The applicant further investigated the possible homodimer formation via re-chromatography of the isolated 30 kDa fraction by SEC under dissociating conditions. Now the corresponding component eluted as a 15 kDa peak in agreement with the findings from SDS-PAGE using non-reduced sample, suggesting a non-covalently associated dimer. Finally, the rFel d 1(2+1) was analysed by surface plasmon resonance with the assumption that a dissociation rate should be possible to calculate if a dimer was attached to the chip. The time-dependent dissociation indicated a tight protein-protein association which was also supported by the fact that no peak corresponding to the size of a monomer could be detected in SEC. Furthermore, the sensorgram obtained suggested a dimer by the roughly 50% decrease in response measured after deactivation.

From a clinical perspective, as well as for epitope probing, it is important to establish accurate levels of allergen-specific antibodies in serum from e.g. cat-allergic patients. The ability to detect allergen specific IgE in serum from 15 cat-allergic patients to rFel d 1(2+1), nFel d 1 and a mixture of Fel d 1 peptides, was evaluated using direct ELISA. No significant difference in response to IgE was detected for recombinant and natural Fel d 1 indicating that all relevant IgE epitopes are present in the rFel d 1(2+1) structure. Also, the results confirm that the carbohydrate side-chain is not crucial for the folding or else serves as an epitope of nFel d 1. The comparable behaviour of rFel d 1 and nFel d 1 was also implied in the competition ELISA.

rFel d 1 and nFel d 1 revealed the same capacity to compete with IgE in serum for binding to microtitre plate bound nFel d 1 in ELISA. The somewhat better homologous inhibition achieved using high concentrations of nFel d 1 is likely to be caused by the inhibition of antibodies present in the serum pool by matching impurities in the nFel d 1 preparation. A mixture of chains 1 and 2 (with no linker) showed significantly lower IgE binding capacity in direct ELISA and a lower specific activity in the inhibition assay, suggesting a distorted protein preparation with fewer exposed epitopes.

The present invention also provides a DNA sequence encoding the rFel d 1 described herein as well as an expression vector capable of expressing the DNA sequence in an operable form. Although exemplified by *E. coli*, the skilled person would be aware that other known cell lines would be capable of preparing rFel d 1. Accordingly the present invention also provides a host cell transformed with the expression vector as described above. A high level expression *E coli* system which produces proteins without the attached carbohydrates has been exemplified herein. However, other known systems may be used which provide for the attached carbohydrates and fall within the scope of the present invention.

rFel d 1 of the present invention may be used for diagnosis and therapy of cat-allergic patients. Specifically the present invention provides a pharmaceutical composition comprising an immunotherapeutically effective amount of the fusion product and/or the homodimer as described herein. The present invention also provides for the use of the fusion product and/or the homodimer as described herein for the preparation of a medicament for the treatment or prevention of cat allergy as well as a method for treating cat allergy, using the fusion product and/or the homodimer as described herein.

The present invention also provides a kit for the diagnosis of a cat allergy comprising the fusion product and/or the homodimer as described herein as well as a method for the diagnosis of an cat allergy comprising obtaining a sample from a subject and combining with the sample the fusion product and/or the homodimer as described herein.

Although the subject treated or diagnosed is preferably a human subject, the subject may be any non-human mammal, such a dog.

EXAMPLES

Example 1

Natural and Recombinant Fel d 1

Standard (see Ausubel, F. A., et al. (eds) (1998) *Current Protocols in Molecular Biology*, John Wiley & Sons, New York) or manufacturers' protocols were used for DNA manipulations. From published amino acid sequences of Fel d 1 chain 1 and 2 (see Chapman, M. D., et al. (1988) *J Immunol* 140, 812-818; Duffort, O. A., et al. (1991) *Mol Immunol* 28, 301-309 and Morgenstern, J. P., et al. (1991) *Proc Natl Acad Sci USA* 88, 9690-9694) synthetic genes were made by PCR-amplification (Eppendorf Mastercycler, Hamburg, Germany) using overlapping DNA-primers from DNA Technology A/S (Århus, Denmark) as shown in Table 1 and which are designated as SEQ ID NOS 5-15. In Table 1, restriction enzyme sites (Nde I and Xho I) are underlined. Forward (F) and reverse (R) primers are indicated.

TABLE 1

| Primer no. | Sequence |
|---|---|
| 1(F) | 5'- gtacatatg g aaatctgccc ggctgttaaa cgtgacgttg acctgttcct gaccggtacc ccggacgaat acgttgaaca ggttg-3' [SEQ ID NO: 5] |
| 2(R) | 5'-ggcagagctt tgtactgagc aacctgttca acgtattcgt ccgggtgagc aacctgttca acgtattc-3' [SEQ ID NO: 6] |
| 3(F) | 5'-tgctcagtac aaagctctgc cggttgttct ggaaaacgct cgtatcctga aaactgcgt tgacgctaaa atgacc-3' [SEQ ID NO: 7] |
| 4(R) | 5'- cctctcgag g cacagcgggg aggtgtagat tttgtccagc agggacagag cgttttcttt gtcttcttcg gtcattttag cgtcaacgc-3' [SEQ ID NO: 8] |
| 5(F) | 5'- gtacatatg g ttaaaatggc tgaaacctgc ccgatcttct acgacgtttt cttcgctgtt gctaacggta acgaac-3' [SEQ ID NO: 9] |
| 6(R) | 5'-ggtacgttcc ggttcggtag cgttaacttt ggtcagggac aggtccagca gcagttcgtt accgttagca acagc-3' [SEQ ID NO: 10] |
| 7(F) | 5'-ctaccgaacc ggaacgtacc gctatgaaaa aaatccagga ctgctacgtt gaaaacggtc tgatctcccg tgttctggac-3' [SEQ ID NO: 11] |
| 8(R) | 5'-gcttcaccca tgcagtcttt ggaggaggag atggtggtca taaccagacc gtccagaaca cgggagatca g-3' [SEQ ID NO: 12] |
| 9(F) | 5'-caaagactgc atgggtgaag ctgttcagaa caccgttgaa gacctgaaac tgaacaccct gggtcgctcg agagg-3' [SEQ ID NO: 13] |

TABLE 1-continued

| Primer no. | Sequence |
|---|---|
| 10(R) | 5'-<u>cctctcgag</u> a cgacccaggg tg-3' [SEQ ID NO: 14] |
| 11(linker) | 5'-cgtttaacag ccgggcagat ttcacgaccc agggtgttca gtttc-3' [SEQ ID NO: 15] |

PCR-reactions (10 µl) containing 1 pmol of each primer, 1-4 for chain 1 and 5-10 for chain 2, using AmpliTaq DNA polymerase (Applied Biosystems, Foster City, Calif., USA) was used. The reactions proceeded for 1.0 min at 94° C., 1.5 min at 65° C. and 2.0 min at 68° C. for 30 cycles. The PCR products were ligated into pT7Blue Blunt Vector, transformed into Nova Blue Single Competent cells using Perfectly Blunt Cloning Kit (Novagen Inc., Madison, Wis., USA). Single colonies were grown in 2.5 ml LB medium containing 100 µg/ml ampicillin and plasmids were purified (Qiagen, GmbH, Hilden, Germany) and cut with the restriction enzymes Nde I and Xho I followed by electrophoretic analysis in 0.3 µg/ml ethidium bromide in 1% agarose gels. Clones with the right size insert (210 and 276 by for chain 1 and 2, respectively) were sequenced (ABI PRISM® 377 DNA Sequencer, Applied Biosystems). Verified plasmids were used as templates to join chains 2 and 1, using primers 4, 5 and 11 as described for the single chains. After sequencing, the fusion constructs were subcloned into pET 20b (Novagen) using the Nde I/Xho I restriction sites and transformed into E coli strain BL-21(DE3)pLysS (Novagen). Clones were selected on LB agar plates with ampicillin (100 mg/l) and chloramphenicol (30 mg/l) and grown in LB medium containing 100 µg/ml ampicillin and 30 µg/ml chloramphenicol. pET 20b inserts of chain 1, chain 2 and rFel d 1(2+1) were sequence verified, (ABI). Expression of protein was induced for 3 h in midlog-phase using 0.4 mM isopropyl-thiogalactoside. The cells were pelleted using a J2-21 centrifuge (Beckman Instruments Inc., Palo Alto, Calif., USA) at 1000×g for 10 min and stored at −20° C. Natural Fel d 1 (>90% pure) from Indoor Biotechnologies (Charlottesville, Va., USA) was used for comparison of immunoreactivity and biological activity between samples.

Example 2

Purification and Characterisation of Recombinant Fel d 1

Protein purification was performed using FPLC, (Amersham Biosciences, Uppsala, Sweden). The same purification protocol was used for all recombinant constructs. The E coli pellets containing the expressed recombinant construct were resuspended in 20 mM Tris/HCl, 0.2 M NaCl, 1 mM EDTA, pH 7A, and disrupted via 8×10 seconds sonication bursts on ice (Soniprep 150 Ultrasonic Disintegrator, Sanyo Gallenkamp, Uxbridge, UK) followed by centrifugtion at 12000×g for 25 min (Beckman Instruments). This procedure was repeated twice, after which the pelleted inclusion body preparation was solubilised in 6 M guanidine/HC, 20 mM Tris/HCl, 0.5 M NaCl, 5 mM imidazole, pH 8.0, and loaded onto a 5 ml Ni$^+$-HiTrap affinity column (Amersham Biosciences) operated at 5 ml/min. The column buffer was changed to 6 M urea, 20 mM Tris/HCl, 0.5 M NaCl, 20 mM imidazole, pH 8.0, and a linear gradient was formed to reach 20 mM Tris/HCl, 0.5 M NaCl, 20 mM imidazole, pH 8.0, after 12 column volumes. The protein was eluted with 20 mM Tris/HCl, 0.5 M NaCl, 0.5 M imidazole, pH 8.0. The enriched rFel d 1 preparation was purified by size exclusion chromatography (SEC) (HiLoad® 16/60 Superdex 200 pg, Amersham Biosciences) equilibrated in PBS and in PBS with 0.1% SDS at 1 ml/min. Molecular weight calibration of the column was carried out using bovine serum albumin (BSA); 67 kDa; ovalbumin, 43 kDa; chymotrypsinogen A, 25 kDa and ribonuclease A, 13.7 kDa (Amersham Biosciences) dissolved in PBS or PBS with 0.1% SDS. The relative elution of reference proteins and rFel d 1(2+1) was calculated according to the formula Kav=Ve-Vo/Vt-Vo (see Scopes, R. K. (1994) *Protein Purification, Principles and Practice*, 3rd ed. Ed. (Cantor, C. R., Ed.), Springer-Verlag, New York, USA). Purified proteins were stored at −80° C. until use.

The protein concentration of rFel d 1(2+1) was analysed by amino acid analysis using a Biochrom 20 Plus ninhydrin-based analyser (Amersham Biosciences) after hydrolysis at 110° C. for 24 h in evacuated tubes with 6 M HCl containing 0.5% (w/v) phenol. The BCA protein assay (Pierce, Rockford, Ill., USA) was sometimes used to estimate the protein concentration. Purity was judged by SDS-PAGE using 15% homogeneous gels and low molecular weight markers (Amersham Biosciences). Samples were denatured at 98° C. for 5 min in SDS sample buffer with or without β-mercaptoethanol (see Ausubel, F. A., et al. (eds). (1998) *Current Protocols in Molecular Biology*, John Wiley & Sons, New York).

Example 3

Electrospray Mass Spectrometry and Determination of Disulfide Bridges

For mass determination of rFel d 1(2+1), the folded protein was dissolved at 27 pmol/µl in 10 mM ammonium acetate (pH 7.3) and was applied to electrospray ionisation (ESI) mass spectrometry (below) via direct infusion using a syringe pump at 2-5 µl min (Harvard Apparatus, Holliston, Mass., USA).

To localise disulfide bridges, 2.7 nmol of the folded rFel d 1(2+1) was dissolved in 10 µl 9 M urea and incubated 30 min under vortex at 45° C. after which 10 µl water was added. Modified trypsin (5 µg, Promega) and 10 µl 0.5 M ammonium bicarbonate (pH 8.0) were added followed by water to yield a final volume of 100 µl. Digestion proceeded overnight under vortex at 37° C. The reaction was quenched by adding 1 µl neat trifluoroacetic acid to the sample which was stored at −20° C. until analysed. Before mass spectrometry, aliquots of the tryptic digest (10 µl) were desalted on µ-$C_{18}$ ZipTips (Millipore, Bedford, Mass., USA) and eluted in 60% acetonitrile containing 1% acetic acid for nano-ESI mass spectrometry. To make sure that no free sulfhydryl groups existed in rFel d 1(2+1), alkylation was carried out on the non-reduced recombinant preparation (5.4 nmol) using iodoacetamide (Sigma, St. Louis, Mo., USA) at 5.5 mM in 20 mM ammonium bicarbonate (pH 8.0) for 15 min at room temperature followed by desalting on µ-$C_4$ ZipTips and nano-ESI mass spectrometry.

Figure 3:
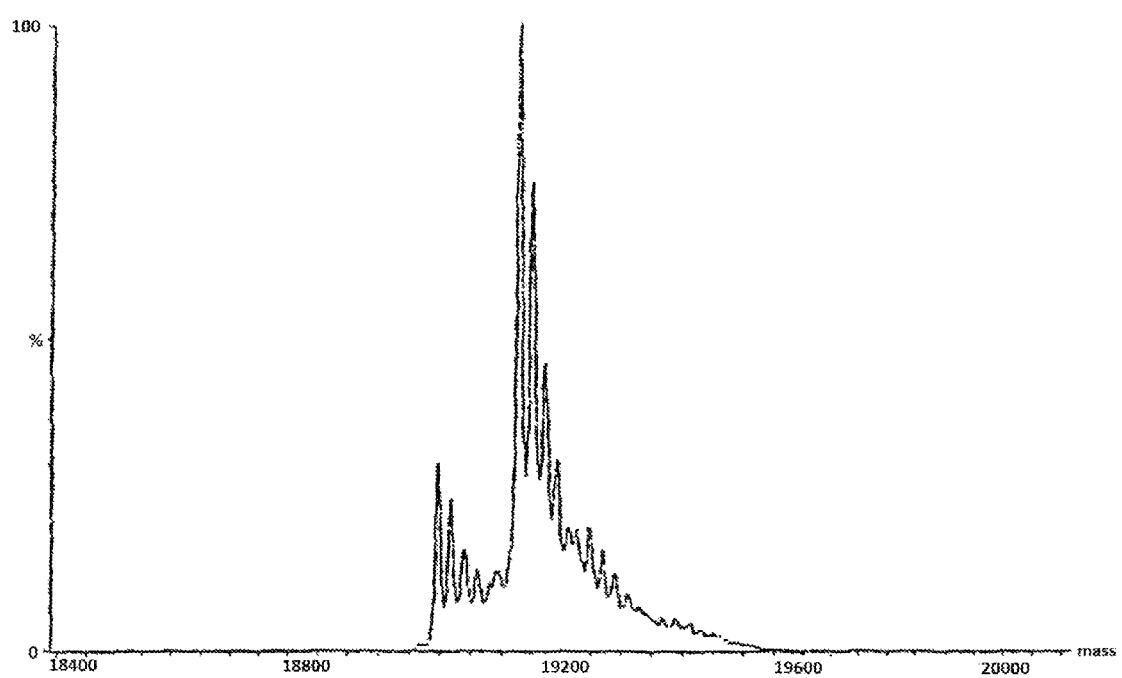
FIG. 3 shows the deconvoluted electrospray mass spectrum from analysis of rFel d 1(2+1)

Mass spectra were recorded using a quadrupole time-of-flight tandem mass spectrometer, Q-TOF (Micromass, Altrincham, UK). The instrument was equipped with an orthogonal sampling ESI-interface (Z-spray, Micromass). Metal-coated nano-ESI needles (Protana, Odense, Denmark) were used and manually opened on the stage of a light microscope to give a spraying orifice of about 5 µm. This resulted in a flow of approximately 20-50 nL/min when a capillary voltage of 0.8-1.2 kV was applied. A nitrogen counter-current drying gas facilitated desolvation. The cone voltage was set at 40 V.

corresponds to the average molecular mass (19183 Da) minus 6 Da, indicating the existence of three disulfide bridges in the structure (FIG. 3). Also seen is an additional peak at 19046 Da, which corresponds to the full-length rFel d 1 without the initiating methionine (Table 1, and residue 0 in FIG. 1 and SEQ ID NO 4). The purity of both the natural and recombinant preparations were >95% as judged by SDS-PAGE (data not shown).

Figure 4:
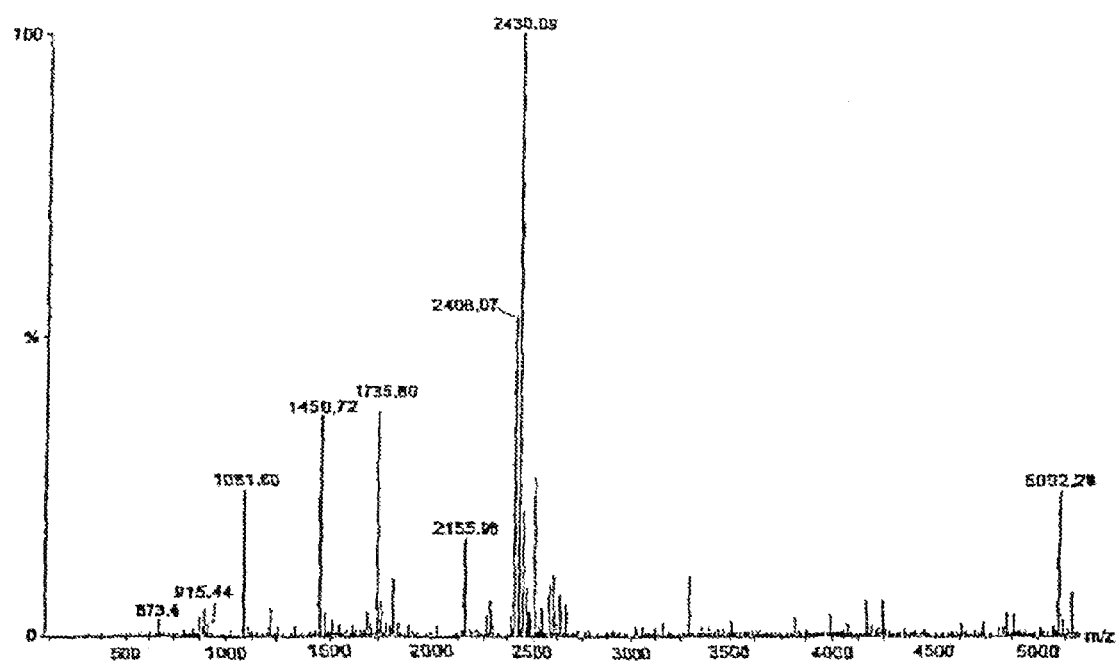
FIG. 4 shows the electrospray mass spectrum from analysis of non-reduced rFel d 1(2+1) digested with trypsin.

The disulfide bridge formation in rFel d 1(2+1) was analysed by nano-ESI mass spectrometry after trypsin digestion of the non-reduced preparation and the results are shown in Table 2 and FIG. 4.

TABLE 2

| Tryptic fragment | Residues | Sequence | Theoretical mass [M + H] | Experimental mass [M + H] |
|---|---|---|---|---|
| T5 | 44-44 | (K)K(I) [SEQ ID NO: 16] | 147.11 | not found |
| T11 | 100-100 | (K)R(D) [SEQ ID NO: 17] | 175.12 | not found |
| T14 | 132-134 | (R)ILK(N) [SEQ ID NO: 18] | 373.28 | not found |
| T1 | 0-2 | (-)MVK(M) [SEQ ID NO: 19] | 377.22 | not found |
| T4 | 40-43 | (R)TAMK(K) [SEQ ID NO: 20] | 450.24 | 450.75 |
| T9 | 87-92 | (K)LNTLGR(E) [SEQ ID NO: 21] | 673.40 | 673.40 |
| T16 | 141-146 | (K)MTEEDK(E) [SEQ ID NO: 22] | 752.31 | not found[a] |
| T3 | 32-39 | (K)VNATEPER(T) [SEQ ID NO: 23] | 915.45 | 915.44 |
| T17 | 147-155 | (K)ENALSLLDK(I) [SEQ ID NO: 24] | 1002.55 | not found[a] |
| T13 | 122-131 | (K)ALPVVLENAR(I) [SEQ ID NO: 25] | 1081.64 | 1081/60 |
| T7 | 58-71 | (R)VLDGLVMTTISSSK(D) [SEQ ID NO: 26] | 1450.78 | 1450.72 |
| T6 | 45-57 | (K)IQDCYVENGLISR(V) [SEQ ID NO: 27] | 2156.01 | 2155.98 |
| T15 | 135-140 | (K)NCVDAK(M) [SEQ ID NO: 28] | | |
| T8 | 72-86 | (K)DCMGEAVQNTVEDLK(L) [SEQ ID NO: 29] | 2408.11 | 2408.07 |
| T10 | 93-99 | (R)EICPAVK(R) [SEQ ID NO: 30] | | |
| T12 | 101-121 | (R)DVDLFLTGTPDEYVEQVAQYK(A) [SEQ ID NO: 31] | 2430.17 | 2430.09 |
| T2 | 3-31 | (K)MAETCPIFYDVFFAVANGNELLLDLSLTK(V) [SEQ ID NO: 32] | 5092.46 | 5092.28 |
| T18 | 156-170 | (K)IYTSPLCLEHHHHHHH(-) [SEQ ID NO: 33] | | |
| T16 + 17 | 141-155 | (K)MTEEDKENALSLLDK(I) [SEQ ID NO: 34] | 1735.86 | 1735.80 |

[a]Not found as a separate fragment. Detected as a part of the larger fragment T16 + T17 with [M + H] 1735.80, resulting from a miscleavage at Lys$_{146}$ which is surrounded by acidic residues, see FIG. 1.

The amino acid sequence and the disulfide bridges as determined by nano-ESI mass spectrometry after tryptic digestion of the *E coli* expressed (His)$_6$-tagged rFel d 1(2+1) fusion protein is shown in FIG. 1 and SEQ ID NO 4. Following column folding and purification by Ni$^+$-chelate chromatography, dominant fractions in SEC with apparent molecular weights of 30 kDa and 51 kDa (FIG. 2) were recovered for further analysis. The 51 kDa component contained inter-chain S—S bonds as shown by a 35 kDa band in non-reducing and a 20 kDa band in reducing SDS-PAGE and was not further analysed (FIG. 2). The 30 kDa fraction which showed a single 30 kDa peak upon re-chromatography, exhibited 16 and 20 kDa bands by non-reducing and reducing SDS-PAGE respectively, (FIG. 2). When subjected to electrospray mass spectrometry, rFel d 1(2+1) revealed a molecular mass of 19177 Da, which Example 4

Homodimer Dissociation Constant Analysis

A BIACORE 2000 instrument (Biacore AB, Uppsala, Sweden) was employed to investigate homodimer formation of rFel d 1(2+1) by evaluation of the decrease in response relative to maximum binding to the chip surface and the associated dissociation constant. rFel d 1(2+1) and for control purpose a monomer protein, BB (see Batard, T., et al. (2000) *J Allergy Clin Immunol* 106, 669-676), were immobilised onto the surfate of CM-5 chips (research grade) via amine coupling to a carboxylated dextran layer using N-hydroxysuccinimide/N-ethyl-N'-(3-diethylaminopropyl)carbodiimide (NHS/EDC) chemistry according to the manufacturers recommendations. The time intervals between surface activation (240-660 s, 35 µl), protein immobilisation (900-1140 s, 20 µl) dissociation phase (1140-1940 s, 67 µl) and surface deactivation (1940-2060 s, 10 µl) were kept constant. In the immobilisation step, 20 µl of a protein solution containing 0.05 µg/µl in 10 mM sodium acetate (pH 4.5) was injected over the NHS/EDC activated surface. After the dissociation phase, the surface was deactivated by injection of 10 pl ethanolarnine. The decrease in percent of protein initially attached to the chip surface was calculated as follows: [Response Units (RU) after protein immobilisation at 1230 s-RU after deactivation/RU after protein immobilisation]×100. All experiments were performed at 25° C. and 5 µl/min. The running buffer was 10 mM Hepes (pH 7.4), 0.15 M NaCl, 3.4 mM EDTA, 0.05% surfactant P20. The dissociation constant analysed at 1230-1235 s was based on the equilibrium responses and calculated using the 3.0 software.

Figure 5:
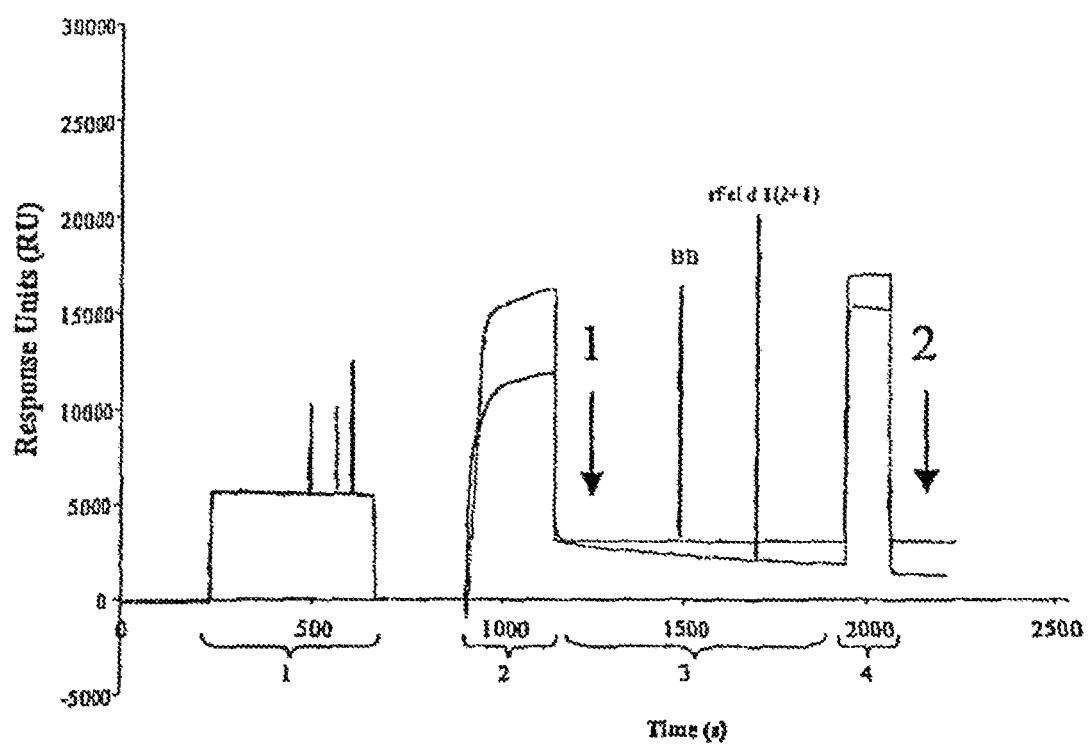
FIG. 5 shows the time-dependent dissociation analysis of immobilised rFel d 1(2+1) by surface plasmon resonance.

The 30-40 kDa molecular size detected for rFel d 1(2+1) suggests a non-covalent dimerisation similar to that exhibited by natural Fel d 1. This was investigated by BIA-CORE® analysis and by SEC under dissociating elution conditions. In the latter case, the 30 kDa rFel d 1(2+1) fraction produced a single peak corresponding to a molecular weight of 15 kDa using PBS with 0.1% SDS in the running buffer (data not shown). The 30 kDa fraction was further analysed by surface plasmon resonance with the assumption that dissociation of the two subunits can be recorded. As a control, monomeric protein, BB (39), was used, (FIG. 5). The rFel d 1(2+1) construct and the BB monomer bound to the sensor chip in a similar manner. The time-dependent decrease in RU after immobilisation of the rFel d 1(2+1) molecule to the chip surface was 53%. In contrast, the BB monomer exhibited a stable association to the chip surface during the same time period. In addition, the dissociation constant was determined shortly after the immobilisation phase to be $8.74 \cdot 10^{-4}$ $s^{-1}$.

Example 5

CD Measurements

CD measurements of the natural and recombinant Fel d 1 were performed in MilliQ water with protein concentrations of $1.56 \times 10^5$ M (here determined using Bio-Rad Protein Assay, Bio-Rad Laboratories, Vienna, Austria). The investigations were carried out on a Jasco J-715 spectropolarimeter (JASCO Labor-und Datentechnik GmbH, Gross-Umstadt, Germany) using a 0.1 cm pathlength cell equilibrated at 20° C. Spectra were recorded with 0.5 nm resolution at a scan speed of 100 nm/min and resulted from averaging 3 scans. The final spectra were baseline-corrected by subtracting the corresponding MilliQ spectra obtained under identical conditions. Results were expressed as the molar mean residue ellipticity [Θ] at a given wavelength. The data were fitted with the secondary structure estimation programs Dicroprot (37) and J-700 (JASCO) using miscellaneous data deconvolution algorithms.

Figure 6:
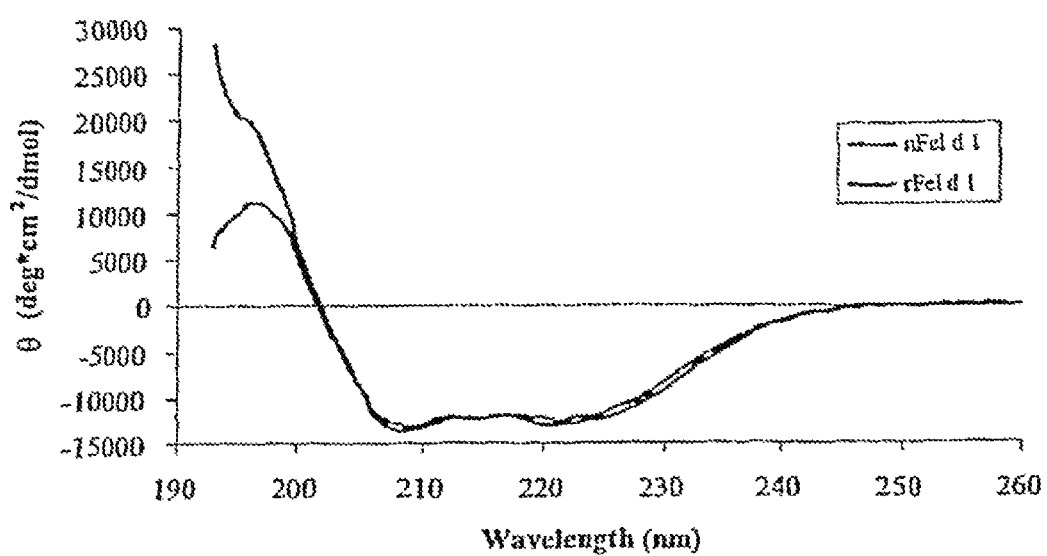
FIG. 6 shows the result of a far-UV CD analysis of rFel d 1 and nFel d 1.

The 20° C. CD spectra of natural and recombinant Fel d 1 are nearly identical, characterised by two minima at 208 nm and 222 nm and a characteristic maximum at about 195 nm (FIG. 6). The shape of the spectrum is indicative for a well folded protein with a significant α-helical secondary structure content. The secondary structure estimation resulting from the fitting procedures yields 35-40% α-helix and 7-16% β-sheet structures with root mean square deviations ($CD_{calc}$-$CD_{exp}$) in the range 4-11%.

Example 6

ELISA Analysis

Serum specimens from 15 individuals were selected on the basis of positive IgE responses to cat dander (range 0.45-38 $kU_A$/L using Pharmacia Diagnostics CAP System, Uppsala, Sweden). For control purpose, a pool of 20 non-cat-allergic patients was used. The serum samples were analysed in duplicates by ELISA for IgE antibody binding to rFel d 1(2+1), nFel d 1 or a mix of rFel d 1 chain 1 and chain 2. The assay was performed as a sequential, solid phase adsorption of allergens, serum sample, primary antibody, antibody conjugate and finally substrate including rinsing four times with 250 µl PBS containing 0.05% Tween 20 (PBS-T) between incubations. If nothing else is stated, all steps were performed at room temperature. Micro titre plates (96 wells, Nunc, Roskilde, Denmark) were coated with 100 µl of rFel d 1(2+1) solution and for comparison also nFel d 1 and an equimolar mixture of chains 1 and 2, to final concentrations of 5 µg/ml in 0.1 M carbonate buffer, pH 9.6. After over-night adsorption at +4° C., the plates were emptied and the remaining protein binding sites were blocked with 200 pl PBS-T containing 1% BSA for 2.5 h at room temperature (20-22° C.). Each serum sample (100 µl) was diluted 1:1 in PBS (duplicates) and incubated for 2 h at room temperature, after which 100 µl rabbit anti-human IgE (Miab, Uppsala, Sweden, diluted 1:2000 (v/v)) was added and incubation was continued for 2 h. Finally, 100 µl goat anti-rabbit, (Dako, Denmark, diluted 1:2000 (v/v)) conjugated to alkaline phosphatase was added and incubation continued for 1 h. Alkaline phosphatase substrate tablets (Sigma 104® Diagnostics, St Louis, Mo., USA) were used and the color reaction monitored at 405 nm was registered in an automated ELISA reader (Multiskan R C, Labsystems, Helsinki, Finland). Competition assay of serum IgE was performed using pooled sera from individuals sensitised to cat with more than 10 $kU_A$/L response to cat dander (mean concentration, 23 $kU_s$/L), (Pharmacia Diagnostics CAP System). Micro-titre plates (96 wells) were coated with 100 µl, 5 µg/ml nFel d 1. Three-fold serial dilutions in PBS-T of rFel d 1(2+1), nFel d 1 and an equimolar mixture of chain 1 and 2 were incubated at a 1:1 volume ratio with the serum pool diluted 1:2 (v/v) in PBS for 2 h at room temperature and thereafter added to the wells. The subsequent steps were as described for the direct ELISA.

Figure 7:
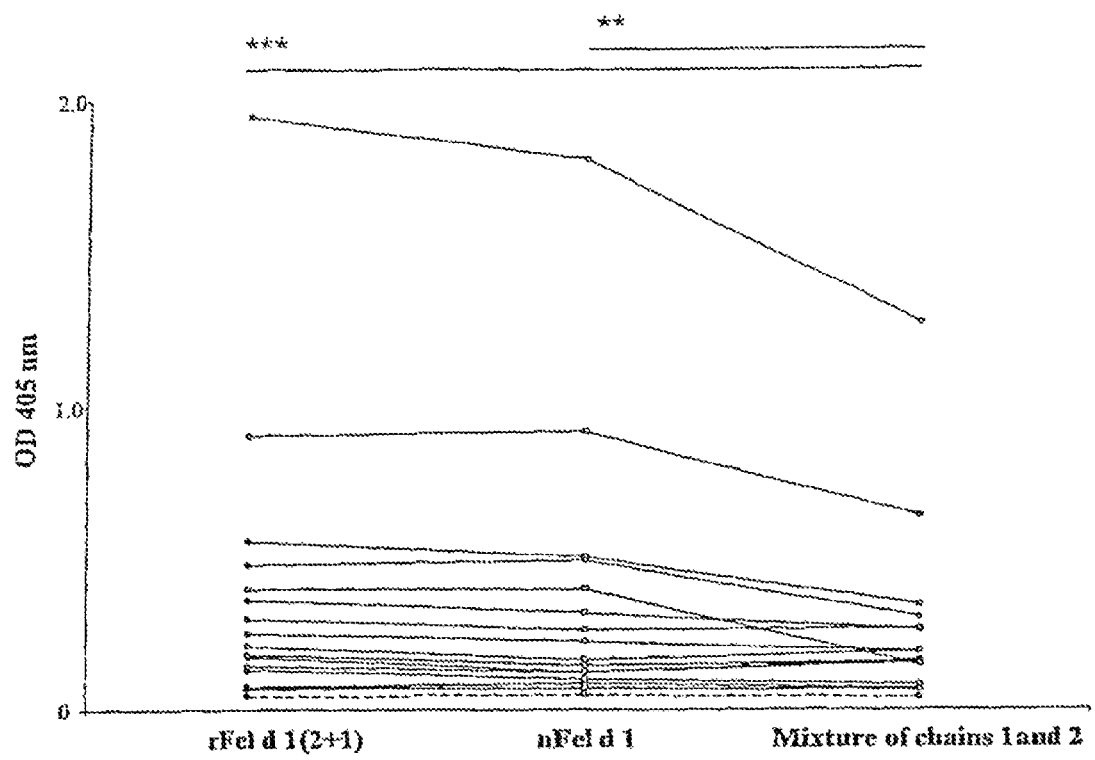
FIG. 7 shows the IgE responses to Fel d 1 in individuals sensitised to cats in direct ELISA.

The diagnostic relevance of a recombinant allergen lies in its ability to bind specifically IgE antibodies in body fluids or in tissues from allergic patients in a manner similar to the natural counterpart. This ability of IgE antibodies in sera from 15 subjects sensitised to cat was compared to detect rFel d 1(2+1), nFel d 1 and Fel d 1 peptide mixture using ELISA. All sera from cat allergic patients showed elevated IgE concentrations compared to a pool of serum from non-cat allergic patients (FIG. 7). Similar responses for rFel d 1(2+1) (optical density (OD) mean, 0.412) and nFel dl (OD mean, 0.384) were observed. There was a significantly lower IgE response to the peptide mixture (OD mean, 0.288) compared to rFel d 1(2+1) and nFel d 1, (ANOVA p<0.001 and p<0.01, respectively).

Figure 8:
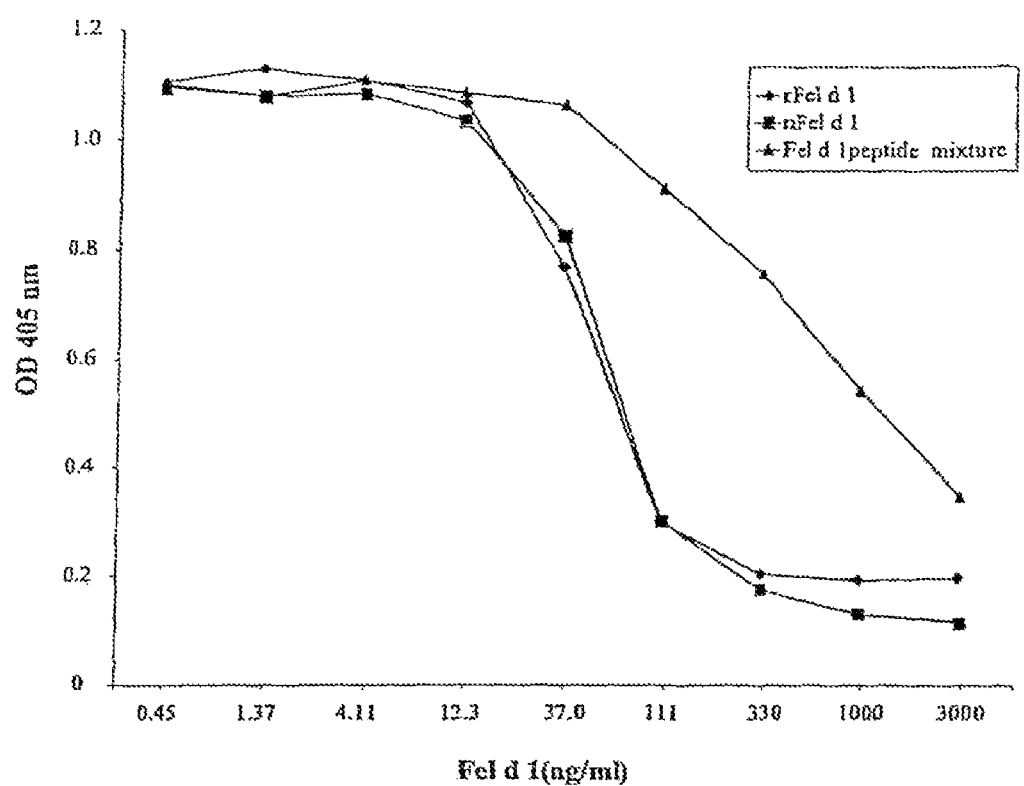
FIG. 8 shows the dose-dependent inhibition of serum IgE from a pool of individuals sensitised to cats.

The capacity of serially diluted rFel d 1(2+1), nFel d 1 and a mixture of chain 1 and chain 2 to compete with the binding of patient IgE to microtitre plate bound nFel d 1 was compared using ELISA. All three Fel d 1 preparations exhibited competing activity. The rFel d 1(2+1) fusion protein inhibited IgE similar as nFel d 1, shown by the proximity and slopes of the dose-dependent inhibition curves in the sensitive range (0.01-0.33 µg/ml), (FIG. 8). The mixture of chain 1 and 2 exhibited more than a 25-fold reduced capacity to compete with IgE binding. By homologous inhibition of nFel d 1, a residual capacity to block IgE was evident using 1 and 3 µg/ml.

Example 7

CD203c Assay

The expression of CD203c was performed as described (see Hauswirth, A. W., et al. (2002) *J Allergy Clin Immunol* 110, 102-109). Briefly, heparinised blood samples were taken from two cat allergic patients. Blood aliquots (100 µl) were incubated with dilutions of recombinant and natural Fel d 1 (1 and 10 µg/ml), anti-IgE antibody (1 µg/ml) or PBS for 15 min (37° C.). After incubation, cells were washed in PBS/EDTA and then incubated with 10 µl of phycoerythrin-labeled CD203c mAb 97A6 (Immunotech, Marseille, France) for 15 min at room temperature. Thereafter, samples were subjected to erythrocyte lysis with 2 ml FACS™ Lysing solution (Becton Dickinson, San Diego, Calif., USA). Cells were then washed, resuspended in PBS, and analysed by two-colour flow cytometry on a FACScan (Becton Dickinson).

Figure 9:
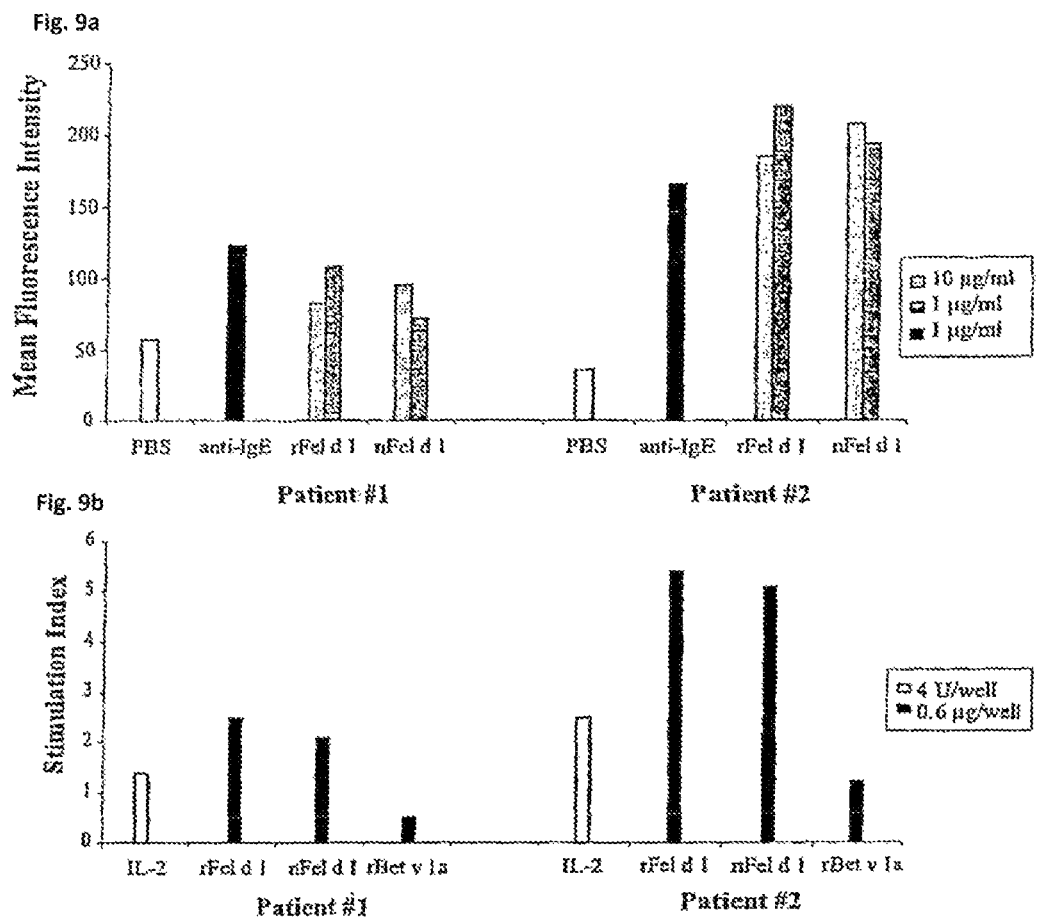
FIG. 9 shows the biologic activity of rFel d 1(2+1) and nFel d 1 in two patients allergic to cats.

The biological activity of rFel d 1(2+1) and nFel d 1 was evaluated in cell preparations donated by two cat allergic patients. The surface marker CD203c is upregulated exclusively on basophils in response to allergen cross-linking of the high affinity IgE receptor, FcεRI (38). The capacity of rFel d 1(2+1) and nFel d 1 to activate expression of CD203c on basophils was similar and compared well to that of anti-IgE, which was used as a positive control (FIG. 9a).

Example 8

Lymphoproliferation Assay

Peripheral blood mononuclear cells (PBMC) were isolated from cat-allergic patients by Ficoll (Amersham Biosciences) density gradient centrifugation. PBMC ($2 \times 10^5$), were cultured in triplicates in 96-well Nunclone plates (Nunc) in 200 µl serum-free Ultra Culture medium (BioWhittaker, Rockland, Me.) supplemented with 2 mM L-glutamin (Sigma), 50 µM β-mercaptoethanol (Sigma) and 0.1 mg gentamicin per ml (Sigma) at 37° C. and 5% $CO_2$ in a humidified atmosphere. Cells were stimulated with different concentrations (5, 2.5, 1.25 and 0.6 µg per well) of rFel d 1, nFel d 1 and for control purpose with recombinant birch pollen allergen Bet v 1, 4 U Interleukin-2 (IL-2) per well (Boehringer Mannheim, Germany) and medium alone. After 6 days of culture, 0.5 µCi per well [$^3$H]thymidine (Amersham Biosciences) was added and 16 h thereafter incorporated radioactivity was measured by liquid scintillation counting using a Microbeta scintillation counter (Wallac ADL, Freiburg, Germany) and mean counts per minute (cpm) were calculated from the triplicates. The stimulation index (SI) was calculated as the quotient of the cpm obtained by antigen or interleukin-2 stimulation and the unstimulated control.

The lymphoproliferative responses after challenge of cultured PBMCs with rFel d 1(2+1) and nFel d 1 were analysed by cell incorporation of [$^3$H]thymidine. Both rFel d 1(2+1) and nFel d 1 exhibited equally good proliferation in contrast to the major birch pollen allergen Bet v 1, which was used as a negative control (FIG. 9b). The T cell proliferation inducing growth factor IL-2 was used as a positive control.

Example 9

Statistical Analysis

Serological results using rFel d 1(2+1), nFel d 1 and the Fel d 1 peptide mixture in the direct ELISA were compared employing ANOVA repeated measures. A p-value <0.05 was considered statistically significant.

The invention claimed is:

1. A recombinant Fel d 1 fusion product comprising a Fel d 1 chain 1 and a Fel d 1 chain 2,
   wherein the Fel d 1 chain 1 consists of (i) the amino acid sequence set forth in SEQ ID NO: 1, or (ii) the amino acid sequence set forth in SEQ ID NO: 1 having one or more amino acid substitutions selected from the group consisting of: Lys29Arg, Lys29Asn, and Val33Ser; and
   wherein Fel d 1 chain 2 consists of
      (i) the amino acid sequence set forth in SEQ ID NO: 2,
      (ii) the amino acid set forth in SEQ ID NO: 2 having one or more amino acid substitutions selected from the group consisting of: Asn19Ser: Gly20Leu, Ile55Val, Arg57Lys, Val58Phe, Glu69Val, Tyr72Asp, Gln79Glu, and Asn88Lys, or
      (iii) the amino acid sequence set forth in SEQ ID NO: 3; and
   wherein the N-terminal amino acid of said Fel d 1 chain 1 is in direct fusion with the C-terminal amino acid of said Fel d 1 chain 2, and wherein said Fel d 1 chain 1 is covalently bonded with said Fel d 1 chain 2 by at least 1 disulfide bridge selected from the group consisting of: 3Cys(1)-73Cys(2), 44Cys(1)-48Cys(2) and 70(Cys(1)-7Cys(2),
   wherein said recombinant fusion product binds IgE from the serum of cat allergic subjects.

2. The recombinant Fel d 1 fusion product of claim 1, wherein the variant of the amino acid sequence set forth in SEQ ID NO:1 comprises two or more amino acid substitutions selected from the group consisting of
   Lys29Arg,
   Lys29Asn, and
   Val33Ser.

3. The recombinant Fel d 1 fusion product of claim 1, wherein the variant of the amino acid sequence set forth in SEQ ID NO:2 comprises two or more amino acid substitutions selected from the group consisting of
   Asn19Ser,
   Gly20 Leu,
   Ile55Val,
   Arg57Lys,
   Val58Phe,
   Glu69Val,
   Tyr72Asp,
   Gln79Glu, and
   Asn88Lys.

4. The recombinant Fel d 1 fusion product of claim 2, wherein the variant of the amino acid sequence set forth in SEQ ID NO:2 comprises two or more amino acid substitutions selected from the group consisting of
   Asn19Ser,
   Gly20 Leu,
   Ile55Val,
   Arg57Lys,
   Val58Phe,
   Glu69Val,
   Tyr72Asp,
   Gln79Glu, and
   Asn88Lys.

5. A recombinant Fel d 1 fusion product comprising a Fel d 1 chain 1 and a Fel d 1 chain 2,
   wherein the Fel d 1 chain 1 consists of (i) the amino acid sequence set forth in SEQ ID NO: 1, or (ii) the amino acid sequence set forth in SEQ ID NO: 1 having one or more amino acid substitutions selected from the group consisting of: Lys29Arg, Lys29Asn, and Val33Ser; and
   wherein Fel d 1 chain 2 consists of
      (i) the amino acid sequence set forth in SEQ ID NO: 2,
      (ii) the amino acid set forth in SEQ ID NO: 2 having one or more amino acid substitutions selected from the group consisting of: Asn19Ser; Gly20Leu, Ile55Val, Arg57Lys, Val58Phe, Glu69Val, Tyr72Asp, Gln79Glu, and Asn88Lys, and
      (iii) the amino acid sequence set forth in SEQ ID NO: 3;
   wherein the N-terminal amino acid of said Fel d 1 chain 1 is in direct fusion with the C-terminal amino acid of said Fel d 1 chain 2, and wherein said Fel d 1 chain 1 is covalently bonded with said Fel d 1 chain 2 by from 1 to 5 disulfide bridges,
   wherein said recombinant fusion product binds IgE from the serum of cat allergic subjects.

6. The recombinant Fel d 1 fusion product of claim 5, wherein said Fel d 1 chain 1 and said Fel d 1 chain 2 are covalently bonded by one, two, or three disulfide bridges, selected from the group consisting of: including 3Cys(1)-73Cys(2), 44Cys(1)-48Cys(2) and 70Cys(1-7Cys(2).

7. A composition comprising an immunotherapeutically effective amount of the recombinant fusion product of claim 1 and a pharmaceutically acceptable carrier, excipient, or diluent.

8. The recombinant fusion product of claim 1, further comprising a methionine residue on the N-terminus.

9. The recombinant fusion product of claim 1, further comprising the sequence Leu-Glu-(His)6 on the C-terminus.

10. The recombinant fusion product of claim 8, further comprising the sequence Leu-Glu-(His)6 on the C-terminus.

11. The fusion product of claim 10, wherein the fusion product has the amino acid sequence set forth in SEQ ID NO: 35.

12. A composition comprising an immunotherapeutically effective amount of the recombinant fusion product of claim 11 and a pharmaceutically acceptable carrier, excipient, or diluent.

13. A kit for the diagnosis of cat allergy comprising the fusion product as claimed in claim 1 and instructions for use of the kit.

14. A kit for the diagnosis of cat allergy comprising the fusion product as claimed in claim 11 and instructions for use of the kit.

15. The recombinant Fel d 1 fusion product of claim 1, wherein Fel d 1 chain 1 consists of the amino acid sequence set forth in SEQ ID NO:1 and wherein Fel d 1 chain 2 consists of the amino acid sequence set forth in SEQ ID NO: 2.

16. A composition comprising an immunotherapeutically effective amount of the recombinant fusion product of claim 15 and a pharmaceutically acceptable carrier, excipient, or diluent.

17. A kit for the diagnosis of cat allergy comprising the fusion product as claimed in claim 15 and instructions for use of the kit.

* * * * *

SEQUENCE LISTING

<160> NUMBER OF SEQ ID NOS: 35

<210> SEQ ID NO 1
<211> LENGTH: 70
<212> TYPE: PRT
<213> ORGANISM: Felis catus

<400> SEQUENCE: 1

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
                20                  25                  30

Val Val Leu Glu Asn Ala Arg Ile Leu Lys Asn Cys Val Asp Ala Lys
            35                  40                  45

Met Thr Glu Glu Asp Lys Glu Asn Ala Leu Ser Leu Leu Asp Lys Ile
        50                  55                  60

Tyr Thr Ser Pro Leu Cys
65                  70

<210> SEQ ID NO 2
<211> LENGTH: 92
<212> TYPE: PRT
<213> ORGANISM: Felis catus

```
<400> SEQUENCE: 2

Val Lys Met Ala Glu Thr Cys Pro Ile Phe Tyr Asp Val Phe Phe Ala
1               5                   10                  15

Val Ala Asn Gly Asn Glu Leu Leu Asp Leu Ser Leu Thr Lys Val
            20                  25                  30

Asn Ala Thr Glu Pro Glu Arg Thr Ala Met Lys Lys Ile Gln Asp Cys
            35                  40                  45

Tyr Val Glu Asn Gly Leu Ile Ser Arg Val Leu Asp Gly Leu Val Met
        50                  55                  60

Thr Thr Ile Ser Ser Ser Lys Asp Cys Met Gly Glu Ala Val Gln Asn
65                  70                  75                  80

Thr Val Glu Asp Leu Lys Leu Asn Thr Leu Gly Arg
                85                  90

<210> SEQ ID NO 3
<211> LENGTH: 90
<212> TYPE: PRT
<213> ORGANISM: Felis catus

<400> SEQUENCE: 3

Val Lys Met Ala Glu Thr Cys Pro Ile Phe Tyr Asp Val Phe Phe Ala
1               5                   10                  15

Val Ala Asn Gly Asn Glu Leu Leu Asp Leu Ser Leu Thr Lys Val
            20                  25                  30

Asn Ala Thr Glu Pro Glu Arg Thr Ala Met Lys Lys Ile Gln Asp Cys
            35                  40                  45

Tyr Val Glu Asn Gly Leu Ile Ser Arg Val Leu Asp Gly Leu Val Met
        50                  55                  60

Ile Ala Ile Asn Glu Tyr Cys Met Gly Glu Ala Val Gln Asn Thr Val
65                  70                  75                  80

Glu Asp Leu Lys Leu Asn Thr Leu Gly Arg
                85                  90

<210> SEQ ID NO 4
<211> LENGTH: 172
<212> TYPE: PRT
<213> ORGANISM: Felis catus

<400> SEQUENCE: 4

Met Val Lys Met Ala Glu Thr Cys Pro Ile Phe Tyr Asp Val Phe Phe
1               5                   10                  15

Ala Val Ala Asn Gly Asn Glu Leu Leu Asp Leu Ser Leu Thr Lys
            20                  25                  30

Val Asn Ala Thr Glu Pro Glu Arg Thr Ala Met Lys Lys Ile Gln Asp
            35                  40                  45

Cys Tyr Val Glu Asn Gly Leu Ile Ser Arg Val Leu Asp Gly Leu Val
        50                  55                  60

Met Thr Thr Ile Ser Ser Ser Lys Asp Cys Met Gly Glu Ala Val Gln
65                  70                  75                  80

Asn Thr Val Glu Asp Leu Lys Leu Asn Thr Leu Gly Arg Glu Ile Cys
                85                  90                  95

Pro Ala Val Lys Arg Asp Val Asp Leu Phe Leu Thr Gly Thr Pro Asp
            100                 105                 110

Glu Tyr Val Glu Gln Val Ala Gln Tyr Lys Ala Leu Pro Val Val Leu
            115                 120                 125
```

-continued

```
Glu Asn Ala Arg Ile Leu Lys Asn Cys Cys Val Asp Ala Lys Met Thr
            130                 135                 140
Glu Glu Asp Lys Glu Asn Ala Leu Ser Leu Leu Asp Lys Ile Tyr Thr
145                 150                 155                 160
Ser Pro Leu Cys Leu Glu His His His His His His
                165                 170

<210> SEQ ID NO 5
<211> LENGTH: 85
<212> TYPE: DNA
<213> ORGANISM: Artificial sequence
<220> FEATURE:
<223> OTHER INFORMATION: oligonucleotide primer with homology to Felis
      catus

<400> SEQUENCE: 5
gtacatatgg aaatctgccc ggctgttaaa cgtgacgttg acctgttcct gaccggtacc    60
ccggacgaat acgttgaaca ggttg                                          85

<210> SEQ ID NO 6
<211> LENGTH: 68
<212> TYPE: DNA
<213> ORGANISM: Artificial sequence
<220> FEATURE:
<223> OTHER INFORMATION: oligonucleotide primer with homology to Felis
      catus

<400> SEQUENCE: 6
ggcagagctt tgtactgagc aacctgttca acgtattcgt ccgggtgagc aacctgttca    60
acgtattc                                                             68

<210> SEQ ID NO 7
<211> LENGTH: 76
<212> TYPE: DNA
<213> ORGANISM: Artificial sequence
<220> FEATURE:
<223> OTHER INFORMATION: oligonucleotide primer with homology to Felis
      catus

<400> SEQUENCE: 7
tgctcagtac aaagctctgc cggttgttct ggaaaacgct cgtatcctga aaactgcgt     60 tgacgctaaa atgacc                                                    76

<210> SEQ ID NO 8
<211> LENGTH: 89
<212> TYPE: DNA
<213> ORGANISM: Artificial sequence
<220> FEATURE:
<223> OTHER INFORMATION: oligonucleotide primer with homology to Felis
      catus

<400> SEQUENCE: 8
cctctcgagg cacagcgggg aggtgtagat tttgtccagc agggacagag cgttttcttt    60
gtcttcttcg gtcattttag cgtcaacgc                                      89

<210> SEQ ID NO 9
<211> LENGTH: 76
<212> TYPE: DNA
<213> ORGANISM: Artificial sequence
<220> FEATURE:
<223> OTHER INFORMATION: oligonucleotide primer with homology to Felis
      catus
```

```
<400> SEQUENCE: 9
gtacatatgg ttaaaatggc tgaaacctgc ccgatcttct acgacgtttt cttcgctgtt    60
gctaacggta acgaac                                                    76

<210> SEQ ID NO 10
<211> LENGTH: 75
<212> TYPE: DNA
<213> ORGANISM: Artificial sequence
<220> FEATURE:
<223> OTHER INFORMATION: oligonucleotide primer with homology to Felis
      catus

<400> SEQUENCE: 10
ggtacgttcc ggttcggtag cgttaacttt ggtcagggac aggtccagca gcagttcgtt    60
accgttagca acagc                                                     75

<210> SEQ ID NO 11
<211> LENGTH: 80
<212> TYPE: DNA
<213> ORGANISM: Artificial sequence
<220> FEATURE:
<223> OTHER INFORMATION: oligonucleotide primer with homology to Felis
      catus

<400> SEQUENCE: 11
ctaccgaacc ggaacgtacc gctatgaaaa aaatccagga ctgctacgtt gaaaacggtc    60
tgatctcccg tgttctggac                                                80

<210> SEQ ID NO 12
<211> LENGTH: 71
<212> TYPE: DNA
<213> ORGANISM: Artificial sequence
<220> FEATURE:
<223> OTHER INFORMATION: oligonucleotide primer with homology to Felis
      catus

<400> SEQUENCE: 12
gcttcaccca tgcagtcttt ggaggaggag atggtggtca taaccagacc gtccagaaca    60
cgggagatca g                                                         71

<210> SEQ ID NO 13
<211> LENGTH: 75
<212> TYPE: DNA
<213> ORGANISM: Artificial sequence
<220> FEATURE:
<223> OTHER INFORMATION: oligonucleotide primer with homology to Felis
      catus

<400> SEQUENCE: 13
caaagactgc atgggtgaag ctgttcagaa caccgttgaa gacctgaaac tgaacaccct    60
gggtcgctcg agagg                                                     75

<210> SEQ ID NO 14
<211> LENGTH: 22
<212> TYPE: DNA
<213> ORGANISM: Artificial sequence
<220> FEATURE:
<223> OTHER INFORMATION: oligonucleotide primer with homology to Felis
      catus

<400> SEQUENCE: 14
cctctcgaga cgacccaggg tg                                             22
```

```
<210> SEQ ID NO 15
<211> LENGTH: 45
<212> TYPE: DNA
<213> ORGANISM: Artificial sequence
<220> FEATURE:
<223> OTHER INFORMATION: oligonucleotide primer with homology to Felis
      catus

<400> SEQUENCE: 15
cgtttaacag ccgggcagat ttcacgaccc agggtgttca gtttc              45

<210> SEQ ID NO 16
<211> LENGTH: 3
<212> TYPE: PRT
<213> ORGANISM: Artificial sequence
<220> FEATURE:
<223> OTHER INFORMATION: polypeptide with homology to Felis catus

<400> SEQUENCE: 16

Lys Lys Ile
1

<210> SEQ ID NO 17
<211> LENGTH: 3
<212> TYPE: PRT
<213> ORGANISM: Artificial sequence
<220> FEATURE:
<223> OTHER INFORMATION: polypeptide with homology to Felis catus

<400> SEQUENCE: 17

Lys Arg Asp
1

<210> SEQ ID NO 18
<211> LENGTH: 5
<212> TYPE: PRT
<213> ORGANISM: Artificial sequence
<220> FEATURE:
<223> OTHER INFORMATION: polypeptide with homology to Felis catus

<400> SEQUENCE: 18

Arg Ile Leu Lys Asn
1               5

<210> SEQ ID NO 19
<211> LENGTH: 4
<212> TYPE: PRT
<213> ORGANISM: Artificial sequence
<220> FEATURE:
<223> OTHER INFORMATION: polypeptide with homology to Felis catus

<400> SEQUENCE: 19

Met Val Lys Met
1

<210> SEQ ID NO 20
<211> LENGTH: 6
<212> TYPE: PRT
<213> ORGANISM: Artificial sequence
<220> FEATURE:
<223> OTHER INFORMATION: polypeptide with homology to Felis catus

<400> SEQUENCE: 20

Arg Thr Ala Met Lys Lys
1               5
```

```
<210> SEQ ID NO 21
<211> LENGTH: 8
<212> TYPE: PRT
<213> ORGANISM: Artificial sequence
<220> FEATURE:
<223> OTHER INFORMATION: polypeptide with homology to Felis catus

<400> SEQUENCE: 21

Lys Leu Asn Thr Leu Gly Arg Glu
1               5

<210> SEQ ID NO 22
<211> LENGTH: 8
<212> TYPE: PRT
<213> ORGANISM: Artificial sequence
<220> FEATURE:
<223> OTHER INFORMATION: polypeptide with homology to Felis catus

<400> SEQUENCE: 22

Lys Met Thr Glu Glu Asp Lys Glu
1               5

<210> SEQ ID NO 23
<211> LENGTH: 10
<212> TYPE: PRT
<213> ORGANISM: Artificial sequence
<220> FEATURE:
<223> OTHER INFORMATION: polypeptide with homology to Felis catus

<400> SEQUENCE: 23

Lys Val Asn Ala Thr Glu Pro Glu Arg Thr
1               5                   10

<210> SEQ ID NO 24
<211> LENGTH: 11
<212> TYPE: PRT
<213> ORGANISM: Artificial sequence
<220> FEATURE:
<223> OTHER INFORMATION: polypeptide with homology to Felis catus

<400> SEQUENCE: 24

Lys Glu Asn Ala Leu Ser Leu Leu Asp Lys Ile
1               5                   10

<210> SEQ ID NO 25
<211> LENGTH: 12
<212> TYPE: PRT
<213> ORGANISM: Artificial sequence
<220> FEATURE:
<223> OTHER INFORMATION: polypeptide with homology to Felis catus

<400> SEQUENCE: 25

Lys Ala Leu Pro Val Val Leu Glu Asn Ala Arg Ile
1               5                   10

<210> SEQ ID NO 26
<211> LENGTH: 16
<212> TYPE: PRT
<213> ORGANISM: Artificial sequence
<220> FEATURE:
<223> OTHER INFORMATION: polypeptide with homology to Felis catus

<400> SEQUENCE: 26

Arg Val Leu Asp Gly Leu Val Met Thr Thr Ile Ser Ser Ser Lys Asp
1               5                   10                  15
```

```
<210> SEQ ID NO 27
<211> LENGTH: 15
<212> TYPE: PRT
<213> ORGANISM: Artificial sequence
<220> FEATURE:
<223> OTHER INFORMATION: polypeptide with homology to Felis catus

<400> SEQUENCE: 27

Lys Ile Gln Asp Cys Tyr Val Glu Asn Gly Leu Ile Ser Arg Val
1               5                   10                  15

<210> SEQ ID NO 28
<211> LENGTH: 8
<212> TYPE: PRT
<213> ORGANISM: Artificial sequence
<220> FEATURE:
<223> OTHER INFORMATION: polypeptide with homology to Felis catus

<400> SEQUENCE: 28

Lys Asn Cys Val Asp Ala Lys Met
1               5

<210> SEQ ID NO 29
<211> LENGTH: 17
<212> TYPE: PRT
<213> ORGANISM: Artificial sequence
<220> FEATURE:
<223> OTHER INFORMATION: polypeptide with homology to Felis catus

<400> SEQUENCE: 29

Lys Asp Cys Met Gly Glu Ala Val Gln Asn Thr Val Glu Asp Leu Lys
1               5                   10                  15

Leu

<210> SEQ ID NO 30
<211> LENGTH: 9
<212> TYPE: PRT
<213> ORGANISM: Artificial sequence
<220> FEATURE:
<223> OTHER INFORMATION: polypeptide with homology to Felis catus

<400> SEQUENCE: 30

Arg Glu Ile Cys Pro Ala Val Lys Arg
1               5

<210> SEQ ID NO 31
<211> LENGTH: 23
<212> TYPE: PRT
<213> ORGANISM: Artificial sequence
<220> FEATURE:
<223> OTHER INFORMATION: polypeptide with homology to Felis catus

<400> SEQUENCE: 31

Arg Asp Val Asp Leu Phe Leu Thr Gly Thr Pro Asp Glu Tyr Val Glu
1               5                   10                  15

Gln Val Ala Gln Tyr Lys Ala
            20

<210> SEQ ID NO 32
<211> LENGTH: 31
<212> TYPE: PRT
<213> ORGANISM: Artificial sequence
<220> FEATURE:
<223> OTHER INFORMATION: polypeptide with homology to Felis catus
```

```
<400> SEQUENCE: 32

Lys Met Ala Glu Thr Cys Pro Ile Phe Tyr Asp Val Phe Phe Ala Val
1               5                  10                  15

Ala Asn Gly Asn Glu Leu Leu Leu Asp Leu Ser Leu Thr Lys Val
            20                  25                  30

<210> SEQ ID NO 33
<211> LENGTH: 16
<212> TYPE: PRT
<213> ORGANISM: Artificial sequence
<220> FEATURE:
<223> OTHER INFORMATION: polypeptide with homology to Felis catus

<400> SEQUENCE: 33

Lys Ile Tyr Thr Ser Pro Leu Cys Leu Glu His His His His His His
1               5                  10                  15

<210> SEQ ID NO 34
<211> LENGTH: 17
<212> TYPE: PRT
<213> ORGANISM: Artificial sequence
<220> FEATURE:
<223> OTHER INFORMATION: polypeptide with homology to Felis catus

<400> SEQUENCE: 34

Lys Met Thr Glu Glu Asp Lys Glu Asn Ala Leu Ser Leu Leu Asp Lys
1               5                  10                  15

Ile

<210> SEQ ID NO 35
<211> LENGTH: 171
<212> TYPE: PRT
<213> ORGANISM: Felis catus

<400> SEQUENCE: 35

Met Val Lys Met Ala Glu Thr Cys Pro Ile Phe Tyr Asp Val Phe Phe
1               5                  10                  15

Ala Val Ala Asn Gly Asn Glu Leu Leu Leu Asp Leu Ser Leu Thr Lys
            20                  25                  30

Val Asn Ala Thr Glu Pro Glu Arg Thr Ala Met Lys Lys Ile Gln Asp
        35                  40                  45

Cys Tyr Val Glu Asn Gly Leu Ile Ser Arg Val Leu Asp Gly Leu Val
    50                  55                  60

Met Thr Thr Ile Ser Ser Ser Lys Asp Cys Met Gly Glu Ala Val Gln
65                  70                  75                  80

Asn Thr Val Glu Asp Leu Lys Leu Asn Thr Leu Gly Arg Glu Ile Cys
                85                  90                  95

Pro Ala Val Lys Arg Asp Val Asp Leu Phe Leu Thr Gly Thr Pro Asp
            100                 105                 110

Glu Tyr Val Glu Gln Val Ala Gln Tyr Lys Ala Leu Pro Val Val Leu
        115                 120                 125

Glu Asn Ala Arg Ile Leu Lys Asn Cys Val Asp Ala Lys Met Thr Glu
    130                 135                 140

Glu Asp Lys Glu Asn Ala Leu Ser Leu Leu Asp Lys Ile Tyr Thr Ser
145                 150                 155                 160

Pro Leu Cys Leu Glu His His His His His
                165                 170
```